US009902812B2

(12) United States Patent
Massey-Brooker et al.

(10) Patent No.: US 9,902,812 B2
(45) Date of Patent: Feb. 27, 2018

(54) CONSUMER GOODS PRODUCT COMPRISING FUNCTIONALISED LIGNIN OLIGOMER

(71) Applicant: The Procter & Gamble Company, Cincinnati, OH (US)

(72) Inventors: Anju Deepali Massey-Brooker, Newcastle upon Tyne (GB); Mauro Vaccaro, Newcastle upon Tyne (GB); Stefano Scialla, Strombeek-Bever (BE); Claudia Crestini, Rome (IT); Heiko Lange, Rome (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/189,011

(22) Filed: Jun. 22, 2016

(65) Prior Publication Data
US 2016/0376408 A1    Dec. 29, 2016

(30) Foreign Application Priority Data

Jun. 24, 2015   (EP) .................................... 15173593

(51) Int. Cl.
| | |
|---|---|
| *A61K 8/97* | (2017.01) |
| *C08G 77/00* | (2006.01) |
| *A61Q 5/02* | (2006.01) |
| *A61Q 5/12* | (2006.01) |
| *A61Q 11/00* | (2006.01) |
| *A61K 8/72* | (2006.01) |
| *A61Q 19/00* | (2006.01) |
| *C07G 1/00* | (2011.01) |
| *C08H 7/00* | (2011.01) |
| *C09G 1/00* | (2006.01) |
| *C11D 3/382* | (2006.01) |
| *C08L 97/00* | (2006.01) |
| *A61K 8/891* | (2006.01) |
| *A61Q 19/02* | (2006.01) |
| *C11D 3/00* | (2006.01) |
| *C11D 3/16* | (2006.01) |
| *C11D 3/37* | (2006.01) |

(52) U.S. Cl.
CPC .............. *C08G 77/80* (2013.01); *A61K 8/72* (2013.01); *A61K 8/891* (2013.01); *A61Q 5/02* (2013.01); *A61Q 5/12* (2013.01); *A61Q 11/00* (2013.01); *A61Q 19/00* (2013.01); *A61Q 19/02* (2013.01); *C07G 1/00* (2013.01); *C08H 6/00* (2013.01); *C08L 97/005* (2013.01); *C09G 1/00* (2013.01); *C11D 3/001* (2013.01); *C11D 3/162* (2013.01); *C11D 3/373* (2013.01); *C11D 3/382* (2013.01); *A61K 2800/57* (2013.01)

(58) Field of Classification Search
None
See application file for complete search history.

(56) References Cited

U.S. PATENT DOCUMENTS

| | | | |
|---|---|---|---|
| 2,352,021 A | 6/1944 | Schubert et al. | |
| 3,912,706 A | 10/1975 | Rachor et al. | |
| 5,512,276 A | 4/1996 | Lang et al. | |
| 6,100,385 A | 8/2000 | Naae et al. | |
| 8,075,637 B2 | 12/2011 | Gizaw et al. | |
| 2003/0139319 A1 | 7/2003 | Scheibel | |
| 2003/0156970 A1 | 8/2003 | Oberkofler et al. | |
| 2008/0125544 A1 | 5/2008 | Yao | |
| 2010/0075878 A1 | 3/2010 | Gizaw et al. | |
| 2011/0114539 A1 | 5/2011 | Stokes et al. | |
| 2013/0233037 A1* | 9/2013 | Adam ...................... C05G 3/06 71/23 |
| 2016/0374921 A1 | 12/2016 | Massey-Brooker et al. | |
| 2016/0374922 A1 | 12/2016 | Massey-Brooker et al. | |
| 2016/0374928 A1 | 12/2016 | Massey-Brooker et al. | |
| 2016/0374935 A1 | 12/2016 | Massey-Brooker et al. | |
| 2016/0375138 A1 | 12/2016 | Massey-Brooker et al. | |

FOREIGN PATENT DOCUMENTS

| | | |
|---|---|---|
| CN | 104 147 977 A | 11/2014 |
| JP | S63 97612 A | 4/1988 |
| JP | H07 215988 A | 8/1995 |
| WO | WO 2010/135804 A1 | 12/2010 |
| WO | WO 2010/135805 A1 | 12/2010 |
| WO | WO 2014/178911 A1 | 11/2014 |

OTHER PUBLICATIONS

Lora, Jairo H., et al., Recent Industrial Applications of Lignin: A Sustainable Alternative to Nonrenewable Materials, Journal of Polymers and the Environment, Apr. 2002, pp. 39-48, vol. 10, Nos. 112, XP-002493248.
Pan, Xuejun, et al., Organosolv Ethanol Lignin from Hybrid Poplar as a Radical Scavenger: Relationship between Lignin Structure, Extraction Conditions, and Antioxidant Activity, J. Agric. Food Chem., 2006, pp. 5806-5813, vol. 54, XP008148495.
Ugartondo, Vanessa, et al., Comparative antioxidant and cytotoxic effects of lignins from different sources, Bioresource Technology, 2008, pp. 6683-6687, vol. 99.
Zhang, Jianfeng, et al., Reductive Degradation of Lignin and Model Compounds by Hydrosilanes, ACS Sustainable Chemistry & Engineering, 2014, pp. 1983-1991, vol. 2.
Uraki, Yasumitsu, et al., Novel Functions of Non-Ionic, Amphiphilic Lignin Derivatives In: ACS Symposium Series, Jan. 1, 2012, pp. 243-254, American Chemical Society/ Oxford University Press, vol. 1107, Chapter 13, XP055235971.

(Continued)

*Primary Examiner* — Brian Gulledge
(74) *Attorney, Agent, or Firm* — John T. Dipre; Steven W. Miller

(57) ABSTRACT

The present invention relates to a consumer goods product comprising a consumer goods product ingredient and a functionalised lignin oligomer, wherein the functionalised lignin oligomer: (a) has an average number of lignin monomers of from 3 to 8; (b) comprises a siloxane functional group; (c) comprises a functionalisation content between 85 and 0.5% lignin (m/m).

20 Claims, No Drawings

(56) References Cited

OTHER PUBLICATIONS

Extended European Search Report; Application No. 15173599.0-1460; dated Jan. 15, 2016, 9 pages.
Extended European Search Report; Application No. 15173603.0-1460; dated Jan. 15, 2016, 8 pages.
Database GNPD [Online], Mintel, Mar. 2009, "Eye Contour Cream", XP002751692, Database accession No. 1102156, *the whole document*.
Database GNPD [Online], Mintel, Apr. 2012, "Aloe Vera Shower Gel", XP002751693, Database accession No. 1765683, *the whole document*.
U.S. Appl. No. 15/189,005, filed Jun. 22, 2016, Massey-Brooker, et al.
U.S. Appl. No. 15/189,007, filed Jun. 22, 2016, Massey-Brooker, et al.
U.S. Appl. No. 15/189,009, filed Jun. 22, 2016, Massey-Brooker, et al.
U.S. Appl. No. 15/189,016, filed Jun. 22, 2016, Massey-Brooker, et al.
U.S. Appl. No. 15/189,019, filed Jun. 22, 2016, Massey-Brooker, et al.

* cited by examiner

CONSUMER GOODS PRODUCT COMPRISING FUNCTIONALISED LIGNIN OLIGOMER

FIELD OF THE INVENTION

The present invention relates to consumer goods products comprising functionalized lignin oligomer.

BACKGROUND OF THE INVENTION

Silicone is incorporated into consumer goods products to provide benefits such as softening and sheen benefits. However, the surface substantivity silicone can be poor, which can lead to poor silicone performance. The inventors have found that functionalizing lignin with silicone in the manner described by the present invention improves the performance of the silicone in the consumer goods product. In addition, the lignin provides anti-oxidant properties, this can be especially preferred for consumer goods products of skin applications.

SUMMARY OF THE INVENTION

The present invention relates to a consumer goods product comprising a consumer goods product ingredient and a functionalised lignin oligomer, wherein the functionalised lignin oligomer: (a) has an average number of lignin monomers of from 3 to 8; (b) comprises a siloxane functional group; (c) comprises a functionalisation content between 85 and 0.5% lignin (m/m).

DETAILED DESCRIPTION OF THE INVENTION

Consumer Goods Product:

The consumer goods product comprises a consumer goods product ingredient and a functionalised lignin oligomer.

The consumer goods product may comprise an emollient and/or humectant.

The consumer goods product may comprise an emulsifier, this may be especially preferred when the lignin oligomer is in the form of an emulsion.

The product may be a skin treatment composition.
The product may be a hair treatment composition.
The product may be an oral care composition.
The product may be an antiseptic cream.
The product may be a shoe polish.
The product may be a detergent composition.

The consumer goods product may comprise chitin and/or chitin derivative.

The consumer goods product is typically selected from: feminine pad; diaper; razor blade strip; hard surface cleaning sheet and/or wipe; and teeth treatment strip.

The consumer goods product is typically selected from: skin cream; skin lotion; shaving preparation gel or foam; handwash laundry detergent; handwash dishwashing detergent; soap bar; liquid handwash soap; body wash; toothpaste; shampoo; and conditioner.

Consumer Goods Product Ingredient:

Suitable consumer goods product ingredients include emollient, humectants, emulsifiers, and any combination thereof.

Functionalised Lignin Oligomer:

The functionalised lignin oligomer: (a) has an average number of lignin monomers of from 3 to 8; (b) comprises a siloxane functional group; (c) comprises a functionalisation content between 85 and 0.5% lignin (m/m).

The functionalised lignin oligomer may be crosslinked, and comprise at least one bonding motif of the following types between the lignin backbone and the functional group:

lignin_backbone-('L')$_m$-'Si'-(L')$_p$-lignin_backbone wherein 'lignin_backbone' is a part of the lignin structural backbone;
wherein 'L' is a linking motif independently selected from the group: —O—, —C(O)O—, —C(O)NR'—, NR'—, and —NR'C(O)NR'—, wherein R' is H or $C_1$-$C_6$ alkyl,
wherein m is 0 or 1;
wherein 'S' is a spacing unit selected from the group: linear or branched, saturated or unsaturated, substituted or unsubstituted $C_2$-$C_{18}$ alkyl chain or a linear or branched, saturated or unsaturated, substituted or unsubstituted secondary hydroxy $C_2$-$C_{18}$ alkyl chain,
wherein p is 0 or 1; and
wherein 'Si' is a polysiloxane.

The functionalised lignin oligomer may be non-crosslinked and comprise a functional group having the structure comprising the functional group:

lignin_backbone-O-L-'Si' wherein 'lignin_backbone' is the lignin structural backbone;
wherein L is a linker; and
wherein 'Si' is a polysiloxane,
wherein L has the chemical structure:

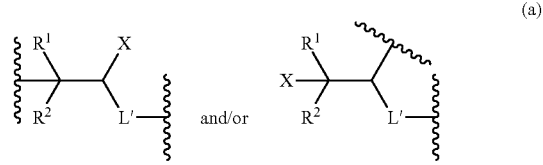

(a)

wherein $R^1$ and $R^2$ are independently selected from H and linear or branched, saturated or unsaturated, substituted or unsubstituted $C_1$ to $C_{18}$ alkyl;
wherein X is independently selected from $R^1$, $R^2$, hydroxyl, amine, ether and ester;
wherein L' is a linking structural motif selected from linear or branched, saturated or unsaturated, substituted or unsubstituted $C_1$ to $C_{18}$ alkyl;
wherein 'Si' is a polysiloxane;
or —C'-L'-|               (b)

wherein —C'— motif is a connecting motif selected from: —C(=O)—, —OC(=O)—, —C(=O)NR'—, wherein R' is selected from H, or $C_1$-$C_6$ alkyl;
wherein L' is a linking structural motif selected from linear or branched, saturated or unsaturated, substituted or unsubstituted $C_1$ to $C_{18}$ alkyl;
wherein 'Si' is a polysiloxane.

The functionalised lignin oligomer may be crosslinked and comprise a functional group having the structure comprising the functional group:

lignin_backbone-O-L-'Si''-L-O-lignin_backbone wherein 'lignin_backbone' is the lignin structural backbone;
wherein 'Si'' is a polysiloxane;
wherein L is a structural motif selected from:

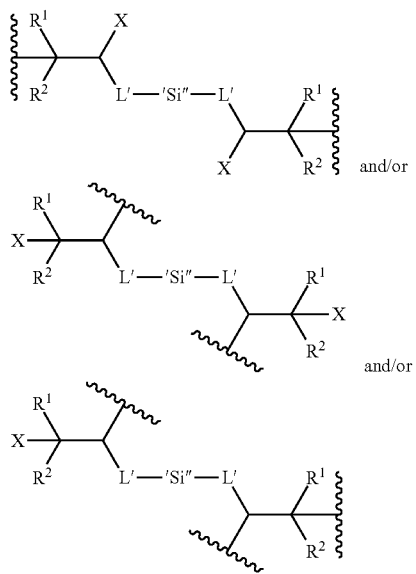

(a)

wherein R¹ and R² are independently selected H and linear or branched, saturated or unsaturated, substituted or unsubstituted $C_1$ to $C_{18}$ alkyl;
wherein X is independently selected from H, linear or branched, saturated or unsaturated, substituted or unsubstituted $C_1$ to $C_{18}$ alkyl, substituted or unsubstituted aromatic or heteroaromatic groups, hydroxyl, amino, ether and ester;
wherein L' is a linking structural motif independently selected from linear or branched, saturated or unsaturated, substituted or unsubstituted $C_1$ to $C_{18}$ alkyl;
wherein 'Si'' is a polysiloxane;
or

  (b)

wherein the C'— motif is a connecting motif selected from: —C(=O)—, —C(=O)O—, —C(=O)NR'—, wherein R' us selected from H, or $C_1$-$C_6$ alkyl;
wherein L' is a linking motif independently selected from linear or branched, saturated or unsaturated, substituted or unsubstituted $C_1$ to $C_{18}$ alkyl;
wherein 'Si'' is a polysiloxane.

The functionalised lignin oligomer may be non-cross linked and comprise a functional group being linked via one of the following structural features:

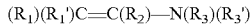

wherein $R_1$, $R_1$' and $R_2$ are independently selected from hydrogen or lignin backbone, wherein at least one of $R_1$, $R_1$' and $R_2$ is lignin backbone,
wherein $R_3$ and $R_3$' are both independently selected from saturated or unsaturated, linear or branched, substituted or unsubstituted $C_1$-$C_{32}$ alkyl, wherein at least one of $R_3$ or $R_3$' is bound to the 'Si' polysiloxane;
or

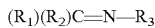

wherein both $R_1$ and $R_2$ are independently selected from hydrogen or lignin backbone, wherein at least one of $R_1$ or $R_2$ is lignin backbone,
wherein $R_3$ is independently selected from saturated or unsaturated, linear or branched, substituted or unsubstituted $C_1$-$C_{32}$ alkyl, wherein $R_3$ is bound to the 'Si' polysiloxane.

The lignin oligomer may comprise at least two different linking motifs.
Preferably, the lignin oligomer has a weight average molecular weight ($\overline{M}_w$) in the range of from 800 Da to 5,000 Da.
Preferably, the lignin oligomer has a number average molecular weight ($\overline{M}_n$) in the range of from 800 Da to 1,200 Da.
Preferably, the lignin oligomer is essentially free of sulphur.
Preferably, the lignin oligomer has an ester content in the range of from 0.0 mmol/g to 0.1 mmol/g.
Preferably, the lignin oligomer is derived from corn, sugar cane, wheat and any combination thereof.

Silicone:
The silicone may be polydimethylsiloxane.
Suitable silicones are selected from the group consisting of silicone polyethers, silicone resins, silicone urethanes, and mixtures thereof provided that these structures contain not more than one reactive motif as decorating feature in a terminal or lateral position with respect to the backbone.
A preferred silicone according to the above definition is a polydialkylsilicone, alternatively a polydimethyl silicone (polydimethyl siloxane or "PDMS"), or a derivative thereof.
Preferably, the silicone meeting the above definitions has a viscosity at a temperature of 25° C. and a shear rate of 1000 s$^{-1}$ in the range of from 10 Pa s to 100 Pa s. Without wishing to be bound by theory, increasing the viscosity of the silicone improves the deposition of the perfume onto the treated surface. However, without wishing to be bound by theory, if the viscosity is too high, it is difficult to process and form the benefit delivery composition.
Other suitable silicones comprising one reactive functional group are selected from an alkyoxylated silicone, preferably ethoxylated silicone, propoxylated silicone, ethoxylated/propoxylated silicone, and any combination thereof as long as these functional groups are compatible with the presence of the for the linking necessary single amino-group present in the same molecule.
Suitable silicone are selected from random or blocky organosilicone polymers having the following formula:

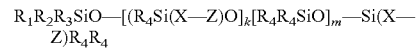

wherein:
k is an integer from 0 to about 200, in one aspect k is an integer from 0 to about 50; when k=0, at least one of $R_1$, $R_2$ or $R_3$ is —X—Z;
m is an integer from 4 to about 5,000; in one aspect m is an integer from about 10 to about 4,000;
in another aspect m is an integer from about 50 to about 2,000;
$R_1$ is selected from the group of moieties of $R_{10}R_{11}N$—$C_1$-$C_{32}$ alkyl, $R_{10}R_{11}N$—$(CH_2$—$CH_2$—$O)_p$ with p being an integer ranging from 1-X and $R_{10}$ and $R_{11}$ being independently selected from H or linear or branched C1-C32 alkyl groups with at least one of them being H, n-$R_{10}R_{11}N$-(n−1)-hydroxy-$C_n$ alkyl with n being an integer from 2 to 32 and $R_{10}$ and $R_{11}$ being independently selected from H or linear or branched C1-C32 alkyl groups with at least one of them being H; alkyl residues mentioned in this list can be substituted, or partly or completely exchanged by C2-C32 alkoxy or C2-C32 substituted alkoxy.
$R_2$ and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy and X—Z;

each $R_4$ is independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy;

each X in said alkyl siloxane polymer comprises a substituted or unsubstituted divalent alkylene radical comprising 2-12 carbon atoms, in one aspect each divalent alkylene radical is independently selected from the group consisting of —(CH$_2$)$_s$— wherein s is an integer from about 2 to about 8, from about 2 to about 4; in one aspect, each X in said alkyl siloxane polymer comprises a substituted divalent alkylene radical selected from the group consisting of: —CH$_2$—CH(OH)—CH$_2$—; —CH$_2$—CH$_2$—CH(OH)—; and

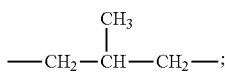

each Z is selected independently from the group consisting of

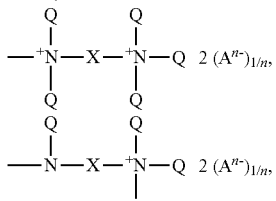

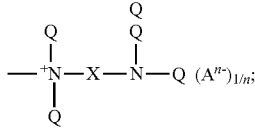

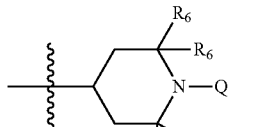

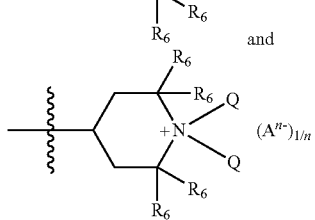

with the proviso that when Z is a quat, Q cannot be an amide, imine, or urea moiety and if Q is an amide, imine, or urea moiety, then any additional Q bonded to the same nitrogen as said amide, imine, or urea moiety must be H or a $C_1$-$C_6$ alkyl, in one aspect, said additional Q is H; for Z A$^{n-}$ is a suitable charge balancing anion. In one aspect A$^{n-}$ is selected from the group consisting of Cl$^-$, Br$^-$, I$^-$, methylsulfate, toluene sulfonate, carboxylate and phosphate; and at least one Q in said organosilicone is independently selected from

—CH$_2$—CH(OH)—CH$_2$—R$_5$;

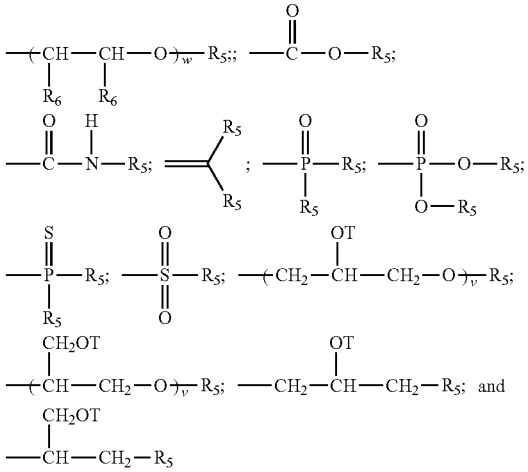

each additional Q in said organosilicone is independently selected from the group comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, —CH$_2$—CH(OH)—CH$_2$—R$_5$;

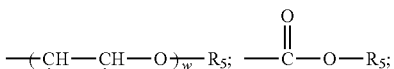
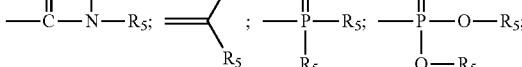
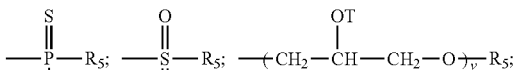
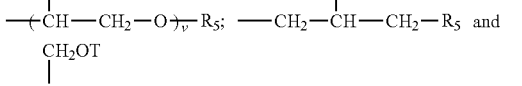

wherein each $R_5$ is independently selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, —(CHR$_6$—CHR$_6$—O—)$_w$-L and a siloxyl residue;

each $R_6$ is independently selected from H, $C_1$-$C_{18}$ alkyl each L is independently selected from —C(O)—R$_7$ or R$_7$;

w is an integer from 0 to about 500, in one aspect w is an integer from about 1 to about 200; in one aspect w is an integer from about 1 to about 50;

each $R_7$ is selected independently from the group consisting of H; $C_1$-$C_{32}$ alkyl; $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl; $C_6$-$C_{32}$ substituted alkylaryl and a siloxyl residue;
each T is independently selected from H, and

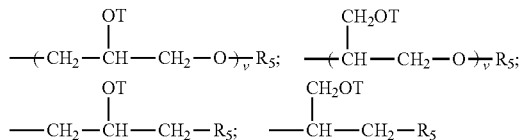

and
wherein each v in said organosilicone is an integer from 1 to about 10, in one aspect, v is an integer from 1 to about 5 and the sum of all v indices in each Q in the said organosilicone is an integer from 1 to about 30 or from 1 to about 20 or even from 1 to about 10.

In another embodiment, the silicone may be chosen from a random or blocky organosilicone polymer having the following formula:

$$R_1R_2R_3SiO-[(R_4Si(X-Z)O]_k[R_4R_4SiO]_m-Si(X-Z)R_4R_4$$

wherein
j is an integer from 0 to about 98; in one aspect j is an integer from 0 to about 48; in one aspect, j is 0;
k is an integer from 0 to about 200; when k=0, at least one of $R_1$, $R_2$ or $R_3$=—X—Z, in one aspect, k is an integer from 0 to about 50
m is an integer from 4 to about 5,000; in one aspect m is an integer from about 10 to about 4,000;
in another aspect m is an integer from about 50 to about 2,000;
$R_1$ is selected from the group of moieties of $R_{10}R_{11}N$—$C_1$-$C_{32}$ alkyl, $R_{10}R_{11}N$—$(CH_2$—$CH_2$—$O)_p$ with p being an integer ranging from 1-X and $R_{10}$ and $R_{11}$ being independently selected from H or linear or branched C1-C32 alkyl groups with at least one of them being H, n-$R_{10}R_{11}N$-(n-1)-hydroxy-$C_{11}$ alkyl with n being an integer from 2 to 32 and $R_{10}$ and $R_{11}$ being independently selected from H or linear or branched C1-C32 alkyl groups with at least one of them being H; alkyl residues mentioned in this list can be substituted, or partly or completely exchanged by C2-C32 alkoxy or C2-C32 substituted alkoxy.
$R_2$ and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy and X—Z;
each $R_4$ is independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy;
each X comprises of a substituted or unsubstituted divalent alkylene radical comprising 2-12 carbon atoms; in one aspect each X is independently selected from the group consisting of —$(CH_2)_s$—O—; —$CH_2$—CH(OH)—$CH_2$—O—;

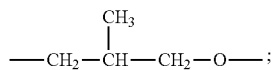

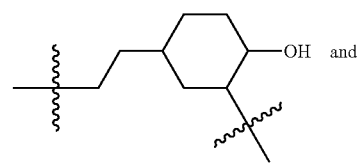

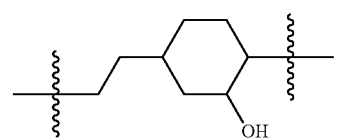

wherein each s independently is an integer from about 2 to about 8, in one aspect s is an integer from about 2 to about 4;

At least one Z in the said organosiloxane is selected from the group consisting of $R_5$;

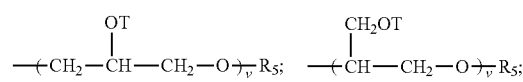

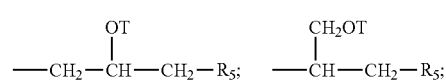

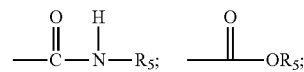

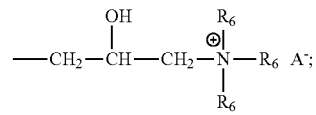

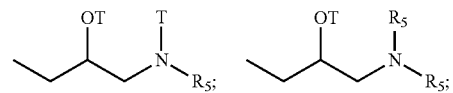

—$C(R_5)_2$O—$R_5$; —$C(R_5)_2$S—$R_5$ and

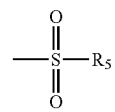

provided that when X is

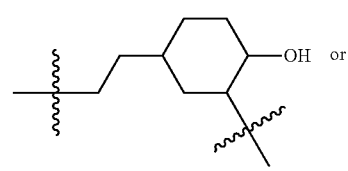

-continued

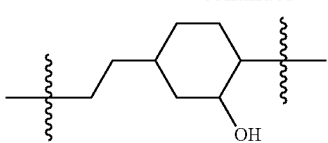

then Z=—OR$_5$ or

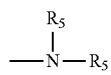

wherein A$^-$ is a suitable charge balancing anion. In one aspect A$^-$ is selected from the group consisting of Cl$^-$, Br$^-$, I$^-$, methylsulfate, toluene sulfonate, carboxylate and phosphate and each additional Z in said organosilicone is independently selected from the group comprising of H, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, R$_5$,

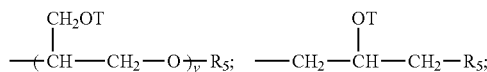

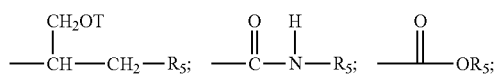

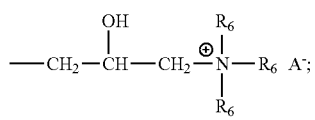

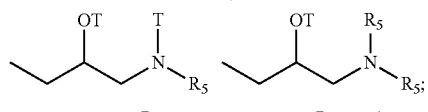

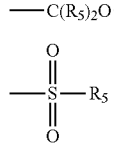

provided that when X is

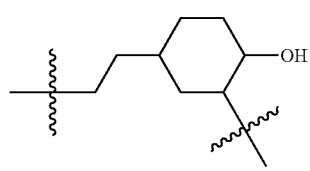

or

-continued

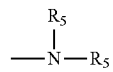

then Z=—OR$_5$ or

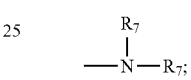

each R$_5$ is independently selected from the group consisting of H; C$_1$-C$_{32}$ alkyl; C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl or C$_6$-C$_{32}$ alkylaryl, or C$_6$-C$_{32}$ substituted alkylaryl, —(CHR$_6$—CHR$_6$—O—)$_w$—CHR$_6$—CHR$_6$-L and siloxyl residue wherein each L is independently selected from —O—C(O)—R$_7$ or —O—R$_7$;

and w is an integer from 0 to about 500, in one aspect w is an integer from 0 to about 200, one aspect w is an integer from 0 to about 50;

each R$_6$ is independently selected from H or C$_1$-C$_{18}$ alkyl;

each R$_7$ is independently selected from the group consisting of H; C$_1$-C$_{32}$ alkyl; C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, and C$_6$-C$_{32}$ substituted aryl, and a siloxyl residue;

each T is independently selected from H;

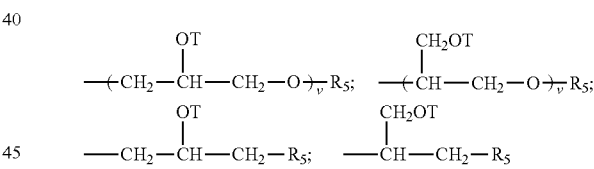

wherein each v in said organosilicone is an integer from 1 to about 10, in one aspect, v is an integer from 1 to about 5 and the sum of all v indices in each Z in the said organosilicone is an integer from 1 to about 30 or from 1 to about 20 or even from 1 to about 10.

A suitable silicone is a blocky cationic organopolysiloxane having the formula:

$$M_w D_x T_y Q_z$$

wherein:

M=[SiR$_1$R$_2$R$_3$O$_{1/2}$], [SiR$_1$R$_2$G$_1$O$_{1/2}$], [SiR$_1$G$_1$G$_2$O$_{1/2}$], [SiG$_1$G$_2$G$_3$O$_{1/2}$], or combinations thereof;

D=[SiR$_1$R$_2$O$_{2/2}$], [SiR$_1$G$_1$O$_{2/2}$], [SiG$_1$G$_2$O$_{2/2}$] or combinations thereof;

T=[SiR$_1$O$_{3/2}$], [SiG$_1$O$_{3/2}$] or combinations thereof;

Q=[SiO$_{4/2}$];

w=is an integer from 1 to (2+y+2z);

x=is an integer from 5 to 15,000;

y=is an integer from 0 to 98;

z=is an integer from 0 to 98;

R₁ is selected from the group of moieties of $R_{10}R_{11}N-C_1-C_{32}$ alkyl, $R_{10}R_{11}N-(CH_2-CH_2-O)_p$ with p being an integer ranging from 1-X and $R_{10}$ and $R_{11}$ being independently selected from H or linear or branched C1-C32 alkyl groups with at least one of them being H, $n-R_{10}R_{11}N-(n-1)$-hydroxy-$C_{11}$ alkyl with n being an integer from 2 to 32 and $R_{10}$ and $R_{11}$ being independently selected from H or linear or branched C1-C32 alkyl groups with at least one of them being H; alkyl residues mentioned in this list can be substituted, or partly or completely exchanged by C2-C32 alkoxy or C2-C32 substituted alkoxy.

R₂ and R₃ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy and X—Z;

only one of the moieties M and D contains only one group R₁ at least one of M, D, or T incorporates at least one moiety G₁, G₂ or G₃, and G₁, G₂, and G₃ are each independently selected from the formula:

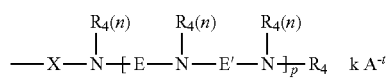

wherein:
X comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, tertiary $C_1$-$C_{32}$ alkyleneamino, tertiary $C_1$-$C_{32}$ substituted alkyleneamino, ring-opened epoxide, and ring-opened glycidyl, with the proviso that if X does not comprise a repeating alkylene oxide moiety then X can further comprise a heteroatom selected from the group consisting of P, N and O;
each R₄ comprises identical or different monovalent radicals selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl;
E comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, tertiary $C_1$-$C_{32}$ alkyleneamino, tertiary $C_1$-$C_{32}$ substituted alkyleneamino, ring-opened epoxide, and ring-opened glycidyl, with the proviso that if E does not comprise a repeating alkylene oxide moiety then E can further comprise a heteroatom selected from the group consisting of P, N, and O;
E' comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, tertiary $C_1$-$C_{32}$ alkyleneamino, tertiary $C_1$-$C_{32}$ substituted alkyleneamino, ring-opened epoxide, and ring-opened glycidyl, with the proviso that if E' does not comprise a repeating alkylene oxide moiety then E' can further comprise a heteroatom selected from the group consisting of P, N, and O;
p is an integer independently selected from 1 to 50;
n is an integer independently selected from 1 or 2;

when at least one of G₁, G₂, or G₃ is positively charged, $A^{-t}$ is a suitable charge balancing anion or anions such that the total charge, k, of the charge-balancing anion or anions is equal to and opposite from the net charge on the moiety G₁, G₂ or G₃, wherein t is an integer independently selected from 1, 2, or 3; and k≤(p*2/t)+1; such that the total number of cationic charges balances the total number of anionic charges in the organopolysiloxane molecule; and wherein at least one E does not comprise an ethylene moiety.

Siloxane Functionalisation of Lignin:
Functionalisation Via Activated Hydroxyl Groups:
Lignin (500 mg) is dissolved in water containing sodium hydroxide (amount corresponding to 1 equivalent (eq.) to total acidic groups in the lignin, i.e., phenolic hydroxyl and carboxylic acid groups. After 1 h of stirring, the suitably terminated siloxane functional, e.g., an epoxide-terminated siloxane functional, is added (depending on the desired technical loading, e.g. in the range of from 0.25 to 10.0 eq. to lignin phenolic hydroxyl groups) and the reaction mixture is stirred at 50° C. overnight. In order to assure appropriate mixing of lignin and terminated siloxane functional in the reaction mixture, additives such as emulsifiers, e.g., non-ionic surfactants, can be used.

After cooling to room temperature and acidifying to pH 2 using 10% (v/v) aqueous hydrogen chloride solution, the resulting suspension is centrifuged (15 min at 500 rpm) to recover the precipitated lignin. The functionalised lignin is then washed 3 times with 50 mL acidified water (pH 2) followed by renewed isolation via centrifugation (15 min at 500 rpm) each time. The final pellet was subsequently freeze-dried. The freeze-dried material is used for analysis and application without any additional manipulation.

Functionalisation Via Keto-Groups:
Lignin, or chemically oxidised lignin, or lignin oxidised biotechnologically using oxidative enzymes, such as, but not exclusively, laccases (EC 1.10.3), polyphenol oxidases (EC 1.14.18) and lipoxygenases (EC 1.13.11) as well as homogenic or heterogenic mixtures thereof, (500 mg) are dissolved or suspended in water or an enzyme-compatible buffer solution in the present of 5% (m/v) of an non-ionic surfactant. the suitably decorated siloxane functional, e.g., an amine-decorated-siloxane-functional, is added and the mixture is stirred for a maximum of 24 hours. In case the reaction is run in the absence of enzymes, the reaction temperature is at 30° C. In case the reaction is run in the presence of one or more enzymes, the temperature is chosen according to a performance study on the enzymatic species revealing the optimum temperature for maximum enzyme activity.

After the desired reaction time, at room temperature, the reaction n mixture is acidified to pH 2 using 10% (v/v) aqueous hydrogen chloride solution. The resulting suspension is centrifuged (15 min at 500 rpm) to recover the precipitated lignin. The functionalised lignin is then washed 3 times with 50 mL acidified water (pH 2) followed by renewed isolation via centrifugation (15 min at 500 rpm) each time. The final pellet was subsequently freeze-dried. The freeze-dried material is used for analysis and application without any additional manipulation.

How to Measure Functionalisation Content:
Evaluation of Bonding Type:
For evaluating the presence of covalent bonding between the silicon and the lignin starting materials, gel permeation chromatography studies are performed.

For the starting materials as well as for the silicon-lignin hybrids, $\overline{M}_n$ and $\overline{M}_w$ are determined, e.g. as described elsewhere. Covalent bonding is indicated by significant augmentations of the signals obtained by the diode array detector at a wavelength of λ=280 nm at elution times at which no signal augmentation was observed for the starting lignin, indicating UV-active species exhibiting molecular weights significantly larger than those observed for the starting lignin under identical analysis conditions.

Quantification of Silicon Content:

Functionalisation Via Activated Hydroxyl Groups:

For evaluating the extend of silicon-lignin hybrid formation, an elemental analysis in the form of a CHNS-analysis was performed as described above using a Carlo-Erba NA 1500 analyzer. Ratios between lignin oligomers and silicon polymers were estimated according to the change in the carbon/hydrogen ratio found in the sample based on the mathematical change caused by the addition of five siloxane monomer units (—Si(CH$_3$)$_2$O—) to the average C$_9$-formula (C$_9$H$_a$O$_b$(OCH$_3$)$_c$)) of the theoretical average monomer of the starting lignin, wherein a is a number between 7.5 and 9.5, b is a number between 2.5 and 6.0, and c is a number between 0.0 and 2.0. Ratios are given in % lignin (m/m).

Functionalisation Via Keto-Groups:

For evaluating the extend of silicon-lignin hybrid formation, an elemental analysis in the form of a CHNS-analysis was performed as described above using a Carlo-Erba NA 1500 analyzer. Ratios between lignin oligomers and silicon polymers were estimated according to the amount of nitrogen found in the sample with respect to the nitrogen content of the polymeric unit of the employed amine group-containing siloxane-functional. Ratios are given in % lignin (m/m).

Method of Measuring Sulphur Content:

The chemical composition of a lignin sample in terms of its carbon (C), hydrogen (H), nitrogen (N) and sulphur (S) content can be determined by elemental analysis in form of a CHNS analysis of at least three different representative samples of a given batch of the respective lignin. Typical sample sizes are 2.0 mg of a lignin sample that was oven-dried at 105° C. until a steady weight was obtained. The samples are placed in aluminum dishes and analyzed using a Carlo-Erba NA 1500 analyzer, using helium as carrier gas. Carbon (C), hydrogen (H), nitrogen (N) and sulphur (S) were detected in form of carbon dioxide, water, nitrogen, and sulphur dioxide, which are chromatographically separated to exit the instrument in the order of nitrogen, carbon dioxide, water, and sulphur dioxide. Quantification is achieved against calibrations using typical standard substances used for the calibration of elemental analysers, such as (bis(5-tert-butyl-2-benzo-oxazol-2-yl) thiophene, based on the peak areas of the chromatograms obtained for each lignin sample.

Method of Measuring $\overline{M}_n$ and $\overline{M}_w$:

The number average molecular weight, $\overline{M}_n$, as well as the weight average molecular weight, $\overline{M}_w$, can be determined using gel permeation chromatography (GPC). Prior to analysis, representative lignin samples are acetobrominated as reported in archival literature (J. Asikkala, T. Tamminen, D. S. Argyropoulos, J. Agric. Food Chem. 2012, 60, 8968-8973.) to ensure complete solubilisation in tetrahydrofuran (THF). 5 mg lignin is suspended in 1 mL glacial acetic acid/acetyl bromide (9:1 v/v) for 2 h. The solvent is then removed under reduced pressure, and the residue is dissolved in HPLC-grade THF and filtered over a 0.45 μm syringe filter prior to injection into a 20 μL sample loop. Typical analysis set-ups resemble the following specific example: GPC-analyses are performed using a Shimadzu instrument consisting of a controller unit (CBM-20A), a pumping unit (LC 20AT), a degasser unit (DGU-20A3), a column oven (CTO-20AC), a diode array detector (SPD-M20A), and a refractive index detector (RID-10A); the instrumental set-up is controlled using the Shimadzu Lab-Solution software package (Version 5.42 SP3). Three analytical GPC columns (each 7.5×30 mm) are connected in series for analyses: Agilent PLgel 5 μm 10000 Å, followed by Agilent PLgel 5 μm 1000 Å and Agilent PLgel 5 μm 500 Å. HPLC-grade THF (Chromasolv®, Sigma-Aldrich) is used as eluent (isocratic at 0.75 mL min$^{-1}$, at 40° C.). Standard calibration is performed with polystyrene standards (Sigma Aldrich, MW range 162-5×106 g mol$^{-1}$), and lower calibration limits are verified/adjusted by the use of synthesized dimeric and trimeric lignin models. Final analyses of each sample is performed using the intensities of the UV signal at λ=280 nm employing a tailor-made MS Excel-based table calculation, in which the number average molecular weight ($\overline{M}_n$) and the weight average molecular weight ($\overline{M}_w$)) is calculated based on the measured absorption (in a.u.) at a given time (min) after corrections for baseline drift and THF-stemming artifacts.

$\overline{M}_n$ is calculated according to the formula $$\overline{M}_n = \frac{\sum w_i}{\sum \frac{w_i}{M_i}}$$

in which $\overline{M}_n$ is the number average molecular weight
$w_i$ is obtained via $$w_i = -h_i \frac{dV}{d(\log M)}$$

with M being molecular weight
hi being the signal intensity of a given log M measurement point
V being the volume of the curve over a given log M interval d(log M).
$M_i$ is a given molecular weight.
The analysis is run in triplicate, and final values are obtained as the standard average.

$\overline{M}_w$ is calculated according to the formula $$\overline{M}_w = \frac{\sum w_i M_i}{\sum w_i}$$

in which $\overline{M}_w$ is the number average molecular weight
$w_i$ is obtained via $$w_i = -h_i \frac{dV}{d(\log M)}$$

with M being the molecular weight
hi being the signal intensity of a given log M measurement point
V being the volume of the curve over a given log M interval d(log M).
$M_i$ is a given molecular weight.
The analysis is run in triplicate, and final values are obtained as the standard average.

Eventually necessary adjustment of $\overline{M}_n$ and $\overline{M}_w$ with respect to the desired applications is achieved by mechanical breaking of polymeric lignin using a ball mill, by chemically or enzymatically polymerising oligomeric lignin.

Method of Measuring Aromatic Hydroxyl and Aliphatic Hydroxyl Content:

Typically, a procedure similar to the one originally published can be used (A. Granata, D. S. Argyropoulos, J. Agric. Food Chem. 1995, 43, 1538-1544). A solvent mixture of pyridine and (CDCl3) (1.6:1 v/v) is prepared under anhydrous conditions. The NMR solvent mixture is stored over molecular sieves (4 Å) under an argon atmosphere. Cholesterol is used as internal standard at a concentration of 0.1 mol/L in the aforementioned NMR solvent mixture. 50 mg of Cr(III) acetyl acetonate are added as relaxation agent to this standard solution.

Ca. 30 mg of the lignin are accurately weighed in a volumetric flask and suspended in 400 μL of the above prepared solvent solution. One hundred microliters of the internal standard solution are added, followed by 100 μL of 2-chloro-4,4,5,5-tetramethyl-1,3,2-dioxaphospholane (Cl-TMDP). The flask is tightly closed, and the mixture is stirred for 120 min at ambient temperature. 31P NMR spectra are recorded using suitable equipment, similar or identical to the following example: On a Bruker 300 MHz NMR spectrometer, the probe temperature is set to 20° C. To eliminate NOE effects, the inverse gated decoupling technique is used. Typical spectral parameters for quantitative studies are as follows: 90° pulse width and sweep width of 6600 Hz. The spectra are accumulated with a delay of 15 s between successive pulses. Line broadening of 4 Hz is applied, and a drift correction is performed prior to Fourier transform. Chemical shifts are expressed in parts per million from 85% $H_3PO_4$ as an external reference. All chemical shifts reported are relative to the reaction product of water with Cl-TMDP, which has been observed to give a sharp signal in pyridine/CDCl3 at 132.2 ppm. To obtain a good resolution of the spectra, a total of 256 scans are acquired. The maximum standard deviation of the reported data is 0.02 mmol/g, while the maximum standard error is 0.01 mmol/g. (A. Granata, D. S. Argyropoulos, J. Agric. Food Chem. 1995, 43, 1538-1544). Quantification on the basis of the signal areas at the characteristic shift regions (in ppm, as reported in A. Granata, D. S. Argyropoulos, J. Agric. Food Chem. 1995, 43, 1538-1544) is done using a tailor-made table calculation in which the abundances, given in mmol/g, of the different delineable phosphitylated hydroxyl groups are determined on the basis of the integral obtained for the signal of the internal standard, that is present in the analysis sample at a concentration of 0.1 m, creating a signal at the interval ranging from 144.5 ppm to 145.3 ppm. The area underneath the peak related to the internal standard is set to a value of 1.0 during peak integration within the standard processing of the crude NMR data, allowing for determining abundances using simple rule-of-proportion mathematics under consideration of the accurate weight of the sample used for this analysis. The analysis is run in triplicate, and final values are obtained as the standard average.

Method of Measuring Hydrolysable Ester Content:

The total ester content of the lignin can be determined by subjecting the lignin to alkaline hydrolysis conditions: Ca. 500 mg of lignin are dissolved in an excess of 1 M sodium hydroxide solution and heated to temperatures of above 70-80° C. for 12 h. The lignin is subsequently precipitated by acidifying the reaction mixture, isolated and freeze-dried.

Ca. 30 mg of the lignin are accurately weighed in a volumetric flask and suspended in 400 μL of the above prepared solvent solution. One hundred microliters of the internal standard solution are added, followed by 100 μL of 2-chloro-4,4,5,5-tetramethyl-1,3,2-dioxaphospholane (Cl-TMDP). The flask is tightly closed, and the mixture is stirred for 120 min at ambient temperature. $^{31}P$ NMR spectra are recorded using suitable equipment under the conditions reported above for the determination of aliphatic and aromatic hydroxyl contents. Quantification of the acid content is done on the basis of the signal intensities at the characteristic shift regions (in ppm) using a tailor-made table calculation referring to the signal of the internal standard. Abundances are typically given in mmol/g. The ester content is obtained as the difference in the abundances of acid groups, aliphatic hydroxyl groups, and aromatic hydroxyl groups found in untreated vs. the lignin treated with sodium hydroxide as outlined above. The analysis is run in triplicate, and final values are obtained as the standard average.

Emollient:

Suitable emollients are silicon based emollients. Silicone-based emollients are organo-silicone based polymers with repeating siloxane (Si O) units. Silicone-based emollients of the present invention are hydrophobic and exist in a wide range of molecular weights. They include linear, cyclic and crosslinked varieties. Silicone oils are generally chemically inert and usually have a high flash point. Due to their low surface tension, silicone oils are easily spreadable and have high surface activity. Examples of silicon oil include: Cyclomethicones, Dimethicones, Phenyl-modified silicones, Alkyl-modified silicones, Silicones resins, Silica. Other emollients useful in the present invention can be unsaturated esters or fatty esters. Examples of unsaturated esters or fatty esters of the present invention include: Caprylic Capric Triglycerides in combination with Bis-PEG/PPG-16/16 PEG/PPG-16/16 Dimethicone and C12-C15 Alkylbenzoate.

The basic reference of the evaluation of surface tension, polarity, viscosity and spreadability of emollient can be found under Dietz, T., Basic properties of cosmetic oils and their relevance to emulsion preparations. SOFW-Journal, July 1999, pages 1-7.

Humectant:

A humectant is a hygroscopic substance used to keep things moist. Typically, it is often a molecule with several hydrophilic groups, most often hydroxyl groups; however, amines and carboxyl groups, sometimes esterified, can be encountered as well (its affinity to form hydrogen bonds with molecules of water is the crucial trait). A humectant typically attracts and retains the moisture in the air nearby via absorption, drawing the water vapour into and/or beneath the organism/object's surface.

Suitable humectants include: Propylene glycol, hexylene glycol, and butylene glycol, Glyceryl triacetate, Neoagarobiose, Sugar alcohols (sugar polyols) such as glycerol, sorbitol, xylitol, maltitol, Polymeric polyols such as polydextrose, *Quillaia*, Urea, Aloe vera gel, MP diol, Alpha hydroxy acids such as lactic acid, Honey, Lithium chloride Emulsifier:

An emulsifier generally helps disperse and suspend a discontinuous phase within a continuous phase in an oil-in-water emulsion. A wide variety of conventional emulsifiers are suitable for use herein. Suitable emulsifiers include: hydrophobically-modified cross-linked polyacrylate polymers and copolymers, polyacrylamide polymers and copolymers, and polyacryloyldimethyl taurates. More preferred examples of the emulsifiers include: acrylates/C10-30 alkyl acrylate cross-polymer having tradenames Pemulen™ TR-1, Pemulen™ TR-2 (all available from Lubrizol); acrylates/steareth-20 methacrylate copolymer with tradename ACRYSOL™ 22 (from Rohm and Hass); polyacrylamide with tradename SEPIGEL 305 (from Seppic).

EXAMPLES

Example 1

The following samples were evaluated by the method described below Sample A is silicone functionalized lignin oligomer in accordance with the present invention. Sample B is unfunctionalised lignin mixed with silicone* (comparative example).

|  | Av. # lignin monomers | Functionalisation | Functionalisation Content |
|---|---|---|---|
| Lignin oligomer of Sample A | 3-8 | Polydimethylsiloxane (PDMS) linked via ether bond | 49% (m/m) |
| Lignin oligomer of Sample B | 3-8 | unfunctionalised | 0% (m/m) |

*Sample B comprises the lignin starting material and the silicone starting material used in the synthesis of the silicone functionalized lignin oligomer of Sample A as a chemically unreactive derivative (i.e. a derivative in which the functional group used to link it to the lignin has been consumed by activated methanol) (i.e. Sample B is the silicone and lignin substrate used to make Sample A).

Preparation of Contact Angle Samples:

Weigh out 0.1 g of silicone functionalised lignin oligomer and disperse in 1 litre of non-ionic based hard surface cleaning product water dispersion (Flash diluted in de-ionised water at the recommended dosage of 4.8 ml/l) and stir it for 15 minutes at 200 rpm at room temperature. Using sodium carbonate, pH was adjusted to pH 10.5. Then, glass slides were dipped for 30 minutes and allowed to dry two hours at room temperature. Following this preparatory procedure contact angle of deionized water on the treated surface was measured using First Ten Angstroms 200 equipment.

Contact Angle Data:

|  | Δ Contact Angle |
|---|---|
| Sample A: silicone functionalised Lignin | 9° |
| Sample B: mixture of unfunctionalised lignin & silicone | 0° |

Sample A in accordance with the present invention showed superior surface modification properties than the comparison example (Sample B).

Example 2

Illustrative Examples

Shampoo Compositions

| Ingredient | Wt. % Product I | Wt. % Product II |
|---|---|---|
| Water | Balance | Balance |
| Cetyl Alcohol | 4.18% | 4.18% |
| Stearyl Alcohol | 7.52% | 7.52% |
| Sodium laureth-3 sulfate (28% Active) | 10.00% | 10.00% |
| Lignin | 0.01% | 1.00% |

Hair Conditioning:

| Components | Wt % New Product I | Wt % New Product II |
|---|---|---|
| Behenyl trimethylammonium methosulfate | 2.97 | — |
| Stearamidopropyl dimethyl amine | — | 3.24 |
| Dicetyl dimethyl ammonium chloride | — | — |
| Cetyl alcohol | 1.01 | 4.25 |
| Stearyl alcohol | 2.53 | 2.93 |
| Benzyl alcohol | 0.4 | 0.4 |
| Deionized Water | Balance | Balance |
| L-glutamic acid | — | 1.04 |
| Preservative (Kathon CG) | 0 | 0 |
| Lignin | 0.01 | 1.00 |
| Amino silicone *3 | 1.5 | 1.5 |
| Perfume | 0.5 | 0.5 |

Hand Dishwashing:

| Examples | Wt % Product I | Wt % Product II |
|---|---|---|
| Alkyl ethoxy sulfate AExS | 16 | 16 |
| Amine oxide | 5.0 | 5.0 |
| C9-11 EO8 | 5 | 5 |
| GLDA | 0.7 | 0.7 |
| Solvent | 1.3 | 1.3 |
| Polypropylene glycol (Mn = 2000) | 0.5 | 0.5 |
| Sodium chloride | 0.8 | 0.8 |
| Lignin | 0.01 | 1.0 |
| Water | Balance | Balance |

Granular Laundry Detergent Compositions Designed for Front-Loading Automatic Washing Machines:

|  | Wt % Product I | Wt % Product II |
|---|---|---|
| Linear alkylbenzenesulfonate | 8 | 8 |
| C12-14 Alkylsulfate | 1 | 1 |
| AE7 | 2.2 | 2.2 |
| $C_{10-12}$ Dimethyl hydroxyethylammonium chloride | 0.75 | 0.75 |
| Crystalline layered silicate (δ-$Na_2Si_2O_5$) | 4.1 | 4.1 |
| Zeolite A | 5 | 5 |
| Citric Acid | 3 | 3 |
| Sodium Carbonate | 15 | 15 |
| Silicate 2R ($SiO_2$:$Na_2O$ at ratio 2:1) | 0.08 | 0.08 |
| Soil release agent | 0.75 | 0.75 |
| Acrylic Acid/Maleic Acid Copolymer | 1.1 | 1.1 |
| Carboxymethylcellulose | 0.15 | 0.15 |
| Protease - Purafect ® (84 mg active/g) | 0.2 | 0.2 |
| Amylase - Stainzyme Plus ® (20 mg active/g) | 0.2 | 0.2 |
| Lipase - Lipex ® (18.00 mg active/g) | 0.05 | 0.05 |

-continued

| | Wt % Product I | Wt % Product II |
|---|---|---|
| Amylase - Natalase ® (8.65 mg active/g) | 0.1 | 0.1 |
| TAED | 3.6 | 3.6 |
| Percarbonate | 13 | 13 |
| Na salt of Ethylenediamine-N,N'-disuccinic acid, (S,S) isomer (EDDS) | 0.2 | 0.2 |
| Hydroxyethane di phosphonate (HEDP) | 0.2 | 0.2 |
| MgSO$_4$ | 0.42 | 0.42 |
| Perfume | 0.5 | 0.5 |
| Suds suppressor agglomerate | 0.05 | 0.05 |
| Soap | 0.45 | 0.45 |
| Sulphonated zinc phthalocyanine (active) | 0.0007 | 0.0007 |
| S-ACMC | 0.01 | 0.01 |
| Lignin | 0.01 | 1.0 |
| Sulfate/Water & Miscellaneous | Balance | Balance |

Beauty Lotion/Cream:

| | Wt % Product I | Wt % Product II |
|---|---|---|
| Water | Balance | Balance |
| Glycerin | 7 | 7 |
| Disodium EDTA | 0.05 | 0.05 |
| Methylparaben | 0.1 | 0.1 |
| Sodium Dehydroacetate | 0.5 | 0.5 |
| Benzyl alcohol | 0.25 | 0.25 |
| GLW75CAP-MP (75% aq. TiO2 dispersion)[1] | 0.5 | 0.5 |
| Palmitoyl-dipeptide[2] | 0.0001 | 0.0001 |
| N-acetyl glucosamine | 2 | 2 |
| Salicylic Acid | 1.5 | 1.5 |
| Isohexadecane | 3 | 3 |
| PPG15 Stearyl Ether | 4 | 4 |
| Isopropyl Isostearate | 1.3 | 1.3 |
| Sucrose polyester | 0.7 | 0.7 |
| Phytosterol | 0.5 | 0.5 |
| Cetyl alcohol | 0.4 | 0.4 |
| Stearyl alcohol | 0.5 | 0.5 |
| Behenyl alcohol | 0.4 | 0.4 |
| PEG-100 stearate | 0.1 | 0.1 |
| Cetearyl glucoside | 0.1 | 0.1 |
| Polyacrylamide/C13-14 isoparaffin/laureth-7 | 2 | 2 |
| Dimethicone/dimethiconol | 2 | 2 |
| Polymethylsilsequioxane | 0.25 | 0.25 |
| Lignin | 0.01 | 1.00 |

Personal Care Product Containing Skin Lightening:

| Component | Wt % Product I | Wt % Product II |
|---|---|---|
| Disodium EDTA | 0.100 | 0.100 |
| Phlorogine BG | 2.000 | 0 |
| deoxyArbutin | 0 | 2.000 |
| Niacinamide | 5.000 | 5.000 |
| Isohexadecane | 3.000 | 3.000 |
| Isopropyl isostearate | 1.330 | 1.330 |
| Sucrose polycottonseedate | 0.670 | 0.670 |
| Polymethylsilsesquioxane | 0.250 | 0.250 |
| Cetearyl glucoside + cetearyl alcohol | 0.200 | 0.200 |
| Behenyl alcohol | 0.400 | 0.400 |
| Ethylparaben | 0.200 | 0.200 |
| Propylparaben | 0.100 | 0.100 |
| Cetyl alcohol | 0.320 | 0.320 |
| Stearyl alcohol | 0.480 | 0.480 |
| Tocopheryl acetate | 0.500 | 0.500 |

-continued

| Component | Wt % Product I | Wt % Product II |
|---|---|---|
| PEG-100 stearate | 0.100 | 0.100 |
| Glycerin | 7.000 | 7.000 |
| Titanium dioxide | 0.604 | 0.604 |
| Polyacrylamide + C13-14 isoparaffin + laureth-7 | 2.000 | 2.000 |
| Panthenol | 1.000 | 1.000 |
| Benzyl alcohol | 0.400 | 0.400 |
| Dimethicone + dimethiconol | 2.000 | 2.000 |
| Lignin | 0.010 | 1.000 |
| Water (to 100 g) | Balance | Balance |

Automatic Dishwashing Cleaning Composition:

| | Powder (wt % based on 19 g portion) | Powder (wt % based on 19 g portion) |
|---|---|---|
| STPP | 34-38 | 34-38 |
| Alcosperse[1] | 7-12 | 7-12 |
| SLF-18 Polytergent[2] | 1-2 | 1-2 |
| Esterified substituted benzene sulfonate[3] | 0.1-6.0 | 0.1-6.0 |
| Polymer[4] | 0.2-6.0 | 0.2-6.0 |
| Sodium perborate monohydrate | 2-6 | 2-6 |
| Carbonate | 20-30 | 20-30 |
| 2.0r silicate | 5-9 | 5-9 |
| Sodium disilicate | 0-3 | 0-3 |
| Enzyme system[5] | 0.1-5.0 | 0.1-5.0 |
| Pentaamine cobalt(III)chloride dichloride salt | 10-15 | 10-15 |
| TAED | 0-3 | 0-3 |
| Perfume, dyes, water and other components | Balance to 100% | Balance to 100% |

| | Liquid (wt % based on 1.9 g portion) | Liquid (wt % based on 1.9 g portion) |
|---|---|---|
| Dipropylene Glycol | 35-45 | 35-45 |
| SLF-19 Polytergent[2] | 40-50 | 40-50 |
| Neodol ® C11EO9 | 1-3 | 1-3 |
| Lignin | 0.01 | 1.0 |
| Dyes, water and other components | Balance | Balance |

[1]such as Alcosperse ® 246 or 247, a sulfonated copolymer of acrylic acid from Alco Chemical Co.
[2]linear alcohol ethoxylate from Olin Corporation
[3]such as those described above
[4]a sulfonated polymer such as those described above
[5]one or more enzymes such as protease, mannaway, natalase, lipase and mixture thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer goods product comprising a consumer goods product ingredient and a functionalised lignin oligomer, wherein the functionalised lignin oligomer:
   (a) has an average number of lignin monomers of from 3 to 8;
   (b) comprises a siloxane functional group;
   (c) comprises a functionalisation content between 85 and 0.5% lignin (m/m).

2. A consumer goods product according to claim 1, wherein the functionalised lignin oligomer is crosslinked, and comprises at least one bonding motif of the following types between the lignin backbone and the functional group:

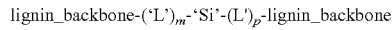

wherein 'lignin_backbone' is a part of the lignin structural backbone;
wherein 'L' is a linking motif independently selected from the group: —O—, —C(O)O—, —C(O)NR'—, NR'—, and —NR'C(O)NR'—, wherein R' is H or $C_1$-$C_6$ alkyl, wherein m is 0 or 1;
wherein 'S' is a spacing unit selected from the group: linear or branched, saturated or unsaturated, substituted or unsubstituted $C_2$-$C_{18}$ alkyl chain or a linear or branched, saturated or unsaturated, substituted or unsubstituted secondary hydroxy $C_2$-$C_{18}$ alkyl chain, wherein p is 0 or 1; and
wherein 'Si' is a polysiloxane.

3. A consumer goods product according to claim 1, wherein the functionalised lignin oligomer is non-crosslinked and comprises a functional group having the structure comprising the functional group:

wherein 'lignin_backbone' is the lignin structural backbone;
wherein L is a linker; and
wherein 'Si' is a polysiloxane,
wherein L has the chemical structure:

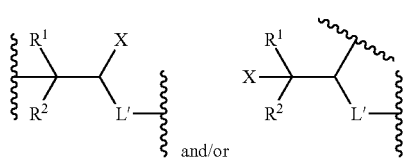

wherein $R^1$ and $R^2$ are independently selected from H and linear or branched, saturated or unsaturated, substituted or unsubstituted $C_1$ to $C_{18}$ alkyl;
wherein X is independently selected from $R^1$, $R^2$, hydroxyl, amine, ether and ester;

wherein L' is a linking structural motif selected from linear or branched, saturated or unsaturated, substituted or unsubstituted $C_1$ to $C_{18}$ alkyl;
wherein 'Si' is a polysiloxane;
or

wherein —C'— motif is a connecting motif selected from: —C(=O)—, —OC(=O)—, —C(=O)NR'—, wherein R' is selected from H, or $C_1$-$C_6$ alkyl;
wherein L' is a linking structural motif selected from linear or branched, saturated or unsaturated, substituted or unsubstituted $C_1$ to $C_{18}$ alkyl;
wherein 'Si' is a polysiloxane.

4. A consumer goods product according to claim 1, wherein the functionalised lignin oligomer is crosslinked and comprises a functional group having the structure comprising the functional group:

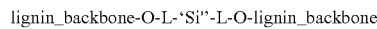

wherein 'lignin_backbone' is the lignin structural backbone;
wherein 'Si'' is a polysiloxane;
wherein L is a structural motif selected from:

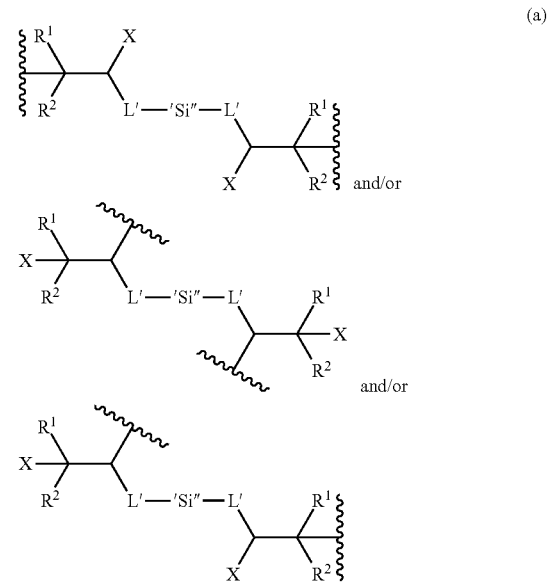

wherein $R^1$ and $R^2$ are independently selected H and linear or branched, saturated or unsaturated, substituted or unsubstituted $C_1$ to $C_{18}$ alkyl;
wherein X is independently selected from H, linear or branched, saturated or unsaturated, substituted or unsubstituted $C_1$ to $C_{18}$ alkyl, substituted or unsubstituted aromatic or heteroaromatic groups, hydroxyl, amino, ether and ester;
wherein L' is a linking structural motif independently selected from linear or branched, saturated or unsaturated, substituted or unsubstituted $C_1$ to $C_{18}$ alkyl;
wherein 'Si'' is a polysiloxane;
or

wherein the C'— motif is a connecting motif selected from: —C(=O)—, —C(=O)O—, —C(=O)NR'—, wherein R' us selected from H, or $C_1$-$C_6$ alkyl;

wherein L' is a linking motif independently selected from linear or branched, saturated or unsaturated, substituted or unsubstituted $C_1$ to $C_{18}$ alkyl;

wherein 'Si" is a polysiloxane.

5. A consumer goods product according to claim 1, wherein the functionalised lignin oligomer is non-cross linked and comprises a functional group being linked via one of the following structural features:

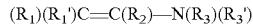

$(R_1)(R_1')C=C(R_2)-N(R_3)(R_3')$ wherein $R_1$, $R_1'$ and $R_2$ are independently selected from hydrogen or lignin backbone, wherein at least one of $R_1$, $R_1'$ and $R_2$ is lignin backbone, wherein $R_3$ and $R_3'$ are both independently selected from saturated or unsaturated, linear or branched, substituted or unsubstituted $C_1$-$C_{32}$ alkyl, wherein at least one of $R_3$ or $R_3'$ is bound to the 'Si' polysiloxane;

or

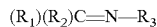

$(R_1)(R_2)C=N-R_3$ wherein both $R_1$ and $R_2$ are independently selected from hydrogen or lignin backbone, wherein at least one of $R_1$ or $R_2$ is lignin backbone, wherein $R_3$ is independently selected from saturated or unsaturated, linear or branched, substituted or unsubstituted $C_1$-$C_{32}$ alkyl, wherein $R_3$ is bound to the 'Si' polysiloxane.

6. A consumer goods product according to claim 1, wherein the lignin oligomer comprises at least two different linking motifs.

7. A consumer goods product according to claim 1, wherein the silicone is polydimethylsiloxane.

8. A consumer goods product according to claim 1, wherein the lignin oligomer has a weight average molecular weight ($\overline{M}_w$) in the range of from 800 Da to 5,000 Da.

9. A consumer goods product according to claim 1, wherein the lignin oligomer has a number average molecular weight ($\overline{M}_n$) in the range of from 800 Da to 1,200 Da.

10. A consumer goods product according to claim 1, wherein the lignin oligomer is essentially free of sulphur.

11. A consumer goods product according to claim 1, wherein the lignin oligomer has an ester content in the range of from 0.0 mmol/g to 0.1 mmol/g.

12. A consumer goods product according to claim 1, wherein the lignin oligomer is derived from corn, sugar cane, wheat and any combination thereof.

13. A consumer goods product according to claim 1, wherein the consumer goods product comprises an emollient and/or humectant.

14. A consumer goods product according to claim 1, wherein the consumer goods product comprises an emulsifier, and wherein the lignin oligomer is in the form of an emulsion.

15. A consumer goods product according to claim 1, wherein the product is a skin treatment composition.

16. A consumer goods product according to claim 1, wherein the product is a hair treatment composition.

17. A consumer goods product according to claim 1, wherein the product is an oral care composition.

18. A consumer goods product according to claim 1, wherein the product is an antiseptic cream.

19. A consumer goods product according to claim 1, wherein the product is a detergent composition.

20. A consumer goods product according to claim 1, wherein the consumer goods product comprises chitin and/or chitin derivatives.

* * * * *